US012806425B2

(12) United States Patent
O'Donoghue et al.

(10) Patent No.: US 12,806,425 B2
(45) Date of Patent: Nov. 24, 2026

(54) BONDING AND CIRCUIT LOCATION FOR IMPLANTABLE MEDICAL DEVICE PCB

(71) Applicant: Cardiac Pacemakers, Inc., St. Paul, MN (US)

(72) Inventors: Robert O'Donoghue, CLonmel (IE); Moira B. Sweeney, St. Paul, MN (US); James Michael English, Cahir (IE); Benjamin J. Haasl, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 320 days.

(21) Appl. No.: 18/398,501

(22) Filed: Dec. 28, 2023

(65) Prior Publication Data

US 2024/0216703 A1 Jul. 4, 2024

Related U.S. Application Data

(60) Provisional application No. 63/435,899, filed on Dec. 29, 2022.

(51) Int. Cl.
*A61N 1/375* (2006.01)

(52) U.S. Cl.
CPC .................................. *A61N 1/3754* (2013.01)

(58) Field of Classification Search
CPC ...... A61N 1/3754; A61N 1/364; A61N 1/362; A61N 1/375; A61N 1/37512; A61N 1/37514; A61N 1/3752; A61N 1/3756; A61N 1/3758
USPC ............................................................ 607/37
See application file for complete search history.

(56) References Cited

U.S. PATENT DOCUMENTS

| | | | | |
|---|---|---|---|---|
| 5,110,034 A * | 5/1992 | Simmonds | H10N 60/80 | 228/208 |
| 2010/0030296 A1* | 2/2010 | Rundle | A61N 1/3754 | 607/37 |
| 2011/0106218 A1* | 5/2011 | Stancer | A61N 1/3718 | 607/63 |
| 2015/0245468 A1* | 8/2015 | Barry | H05K 3/32 | 174/257 |

FOREIGN PATENT DOCUMENTS

WO WO-2019200046 A1 * 10/2019 ........... A61B 5/6868

* cited by examiner

*Primary Examiner* — Aaron F Roane

(74) *Attorney, Agent, or Firm* — Nelson Mullins Riley & Scarborough LLP

(57) ABSTRACT

An implantable medical device can include a housing including electronic devices within the housing; a header attached to the housing and including one or more bores; and a feedthrough assembly between the housing and the header; wherein the electronic devices include a PCB electronically connected to the header by a feedthrough wire running from the feedthrough assembly to the PCB, wherein the feed-through wire extends through the PCB and includes a dome-shaped end adapted to be attached to a connector ribbon by laser wire bonding.

20 Claims, 4 Drawing Sheets

BONDING AND CIRCUIT LOCATION FOR IMPLANTABLE MEDICAL DEVICE PCB

CLAIM OF PRIORITY

This application claims the benefit of U.S. Provisional Application No. 63/435,899, filed on Dec. 29, 2022, which is hereby incorporated by reference in its entirety.

TECHNICAL FIELD

Various embodiments described herein relate to apparatus, systems, and methods associated with implantable medical devices.

BACKGROUND

An ambulatory medical device, such as an implantable medical device (IMD), can be configured for implant in a subject, such as a patient. An IMD can be configured to be coupled to a patient's heart such as via one or more implantable leads. Such an IMD can obtain diagnostic information or generate therapy to be provided to the patient, such as via the coupled implantable lead.

In one configuration, IMDs have a header that is coupled to a housing that houses much of the electronics of the IMD. The header can be used to couple a conductor of the implantable lead with circuitry within the implantable device. The header is electrically connected to the electronics in the housing by one or more feedthrough wires attached to a printed circuit board (PCB) within the housing. The PCB can be utilized to hold a variety of electronic components. There is a need to ensure accurate placement of the PCB components in regard to the space limitations and to provide robust and easy to make connections between the various components.

SUMMARY

Example 1 can include subject matter such as an implantable device. The implantable medical device can include a housing including electronic devices within the housing; a header attached to the housing and including one or more bores; and a feedthrough assembly between the housing and the header; wherein the electronic devices include a PCB electronically connected to the header by a feedthrough wire running from the feedthrough assembly to the PCB, wherein the feedthrough wire extends through the PCB and includes a dome-shaped end adapted to be attached to a connector ribbon by laser wire bonding.

In Example 2, the subject matter of Example 1 can optionally include the feedthrough wire including a platinum feedthrough wire.

In Example 3, the subject matter of any one or more of Examples 1-2 can optionally include the dome-shaped end of the feedthrough wire including a hemisphere shape at a distal end of the feedthrough wire.

In Example 4, the subject matter of any one or more of Examples 1-3 can optionally include the feedthrough wire extending from a bottom surface of the PCB and extending through a through-hole of the PCB such that the dome-shaped end is exposed at an upper surface of the PCB.

In Example 5, the subject matter of any one or more of Examples 1-4 can optionally include the dome-shaped end being configured to define a known contact point for the connector ribbon.

In Example 6, the subject matter of any one or more of Examples 1-5 can optionally include the connector ribbon including an Nb connector ribbon.

In Example 7, the subject matter of any one or more of Examples 1-6 can optionally include a second end of the Nb connector ribbon being connected to a contact pad on the PCB.

In Example 8, the subject matter of any one or more of Examples 1-7 can optionally include a second end of the connector ribbon being bonded directly to a surface contact of the PCB.

In Example 9, the subject matter of any one or more of Examples 1-8 can optionally include the surface contact includes a copper substrate with a gold-coated contact surface.

In Example 10, the subject matter of any one or more of Examples 1-9 can optionally include a plurality of vias running through surface contact and the PCB.

Example 11 can include an implantable medical device including a housing including electronic devices within the housing; a header attached to the housing and including one or more bores; and a feedthrough assembly between the housing and the header; wherein the electronic devices include a PCB electronically connected to the header by a feedthrough wire running from the feedthrough assembly to the PCB, wherein the feedthrough wire is attached to a contact on the PCB by a connector ribbon, the connector ribbon including Nb.

In Example 12, the subject matter of any one or more of Examples 1-11 can optionally include the connector ribbon being bonded directly to a surface contact of the PCB.

In Example 13, the subject matter of any one or more of Examples 1-12 can optionally include the surface contact including a copper substrate with a gold-coated contact surface.

In Example 14, the subject matter of any one or more of Examples 1-13 can optionally include a plurality of vias running through the surface contact and the PCB.

In Example 15, the subject matter of any one or more of Examples 1-14 can optionally include the connector ribbon being bonded to the surface contact by laser ribbon bonding.

In Example 16, the subject matter of any one or more of Examples 1-15 can optionally include the feedthrough wire being attached to the connector ribbon at a dome-shaped end of the feedthrough wire.

Example 17 can include subject matter such as a method of attaching a feedthrough wire to a connector ribbon. The method can include extending a feedthrough wire through a through-hole of a PCB, the feedthrough wire including a dome-shaped end; and bonding a connector ribbon to the dome-shaped end.

In Example 18, the subject matter of any one or more of Examples 1-17 can optionally include the bonding including laser wire bonding.

In Example 19, the subject matter of any one or more of Examples 1-18 can optionally include connecting the connector ribbon directly to a surface contact of the PCB, wherein the connector ribbon includes Nb and the surface contact includes a copper substrate with a gold-coated contact surface.

In Example 20, the subject matter of any one or more of Examples 1-19 can optionally include a plurality of vias running through surface contact and the PCB.

In Example 21, subject matter (e.g., a system or apparatus) may optionally combine any portion or combination of any portion of any one or more of Examples 1-20 to comprise "means for" performing any portion of any one or more of the functions or methods of Examples 1-20, or at least one "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

DETAILED DESCRIPTION

In the following detailed description, reference is made to the accompanying drawings that form a part hereof and in which are shown, by way of illustration, specific embodiments in which the invention may be practiced. These embodiments are described in sufficient detail to enable those skilled in the art to practice the invention. Other embodiments may be utilized and structural, logical, and electrical changes may be made.

Figure 1:
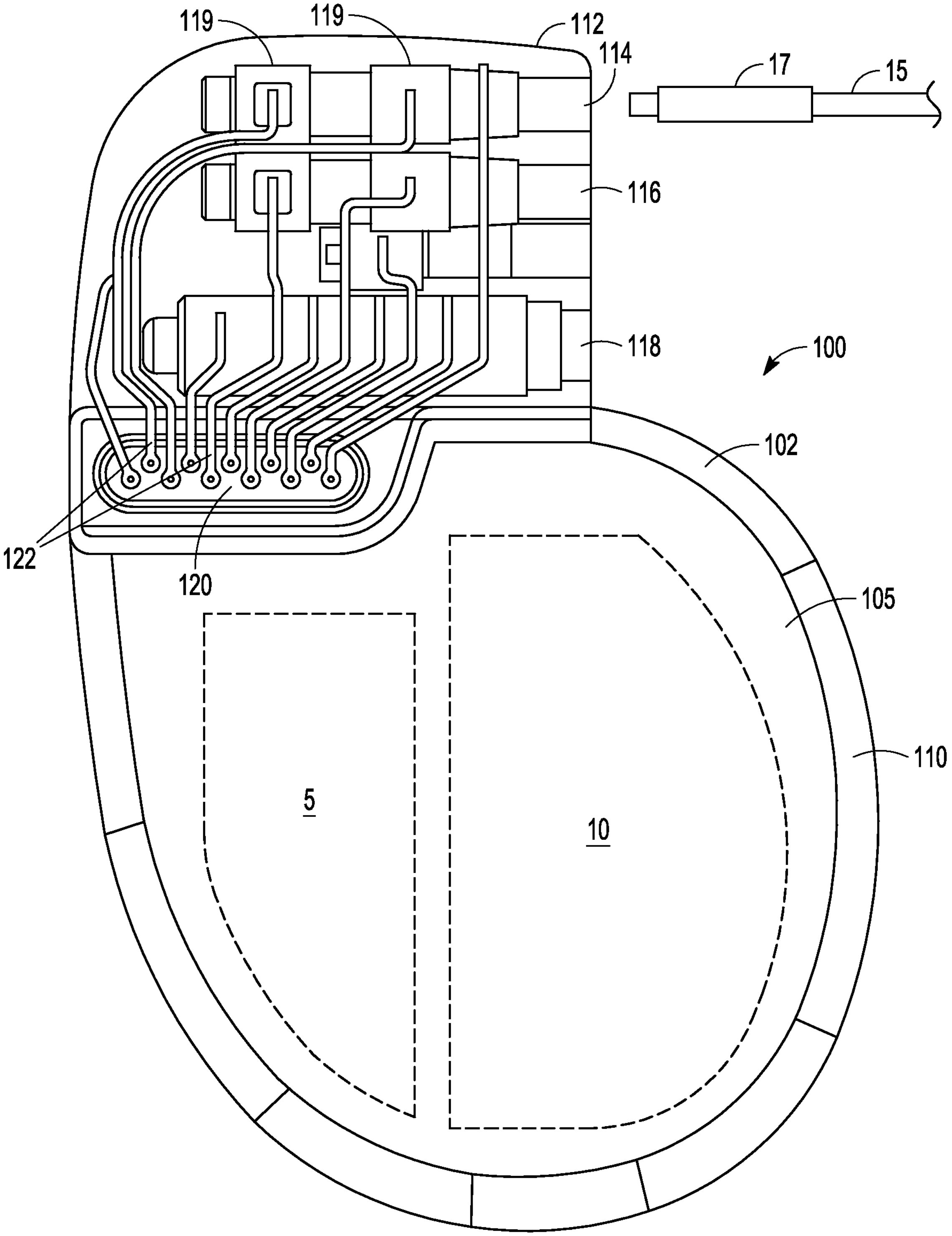
FIG. 1 shows an example implantable medical device, in accordance with one embodiment.

FIG. 1 shows an implantable system 100 including an implantable medical device 102, in accordance with one embodiment. The implantable medical device 102 includes a pulse generator 105 and at least one implantable lead 15. The pulse generator 105 includes a housing 110 and a header 112 mounted to the housing 110. The pulse generator 105 can be implanted into a subcutaneous pocket made in the wall of a patient's chest. Alternatively, the pulse generator 105 can be placed in a subcutaneous pocket made in the abdomen, or in other locations. The pulse generator 105 can include electronic devices such as a power supply 5 including a battery, a capacitor, and other components housed in the housing 110. The pulse generator 105 can further include other electronic devices including electronic components 10, such as microprocessors to provide processing, evaluation, and to deliver electrical shocks and pulses of different energy levels and timing for defibrillation, cardioversion, and pacing to a heart in response to cardiac arrhythmia including fibrillation, tachycardia, heart failure, and bradycardia.

The header 112 can include one or more bores 114, 116, 118 to receive the implantable lead 15. The implantable lead 15 can include electrodes on a distal end to provide therapy to a body and include a terminal pin 17 on a proximal end to couple to one of the bores 114, 116, 118. At least one electrical conductor is disposed within the lead 15 and extends from the proximal end to the electrode. The electrical conductor carries electrical currents and signals between the pulse generator 105 and the electrode.

Contacts on the terminal pin 17 can electrically contact electrical one or more contacts 119 within the bores 114, 116, 118 to allow signals and therapy to be delivered to and from electrodes in the body to the electronics 5, 10 within the housing 110. The contacts 119 can be connected by a plurality of wires 122 to a feedthrough assembly 120 to electrically communicate between the lead 15 and the electronics within the housing 110.

As noted, the pulse generator 105 includes electronic devices including electronic components 10, such as microprocessors to provide processing, evaluation, and to deliver electrical shocks and pulses of different energy levels and timing for various conditions.

Figure 2:
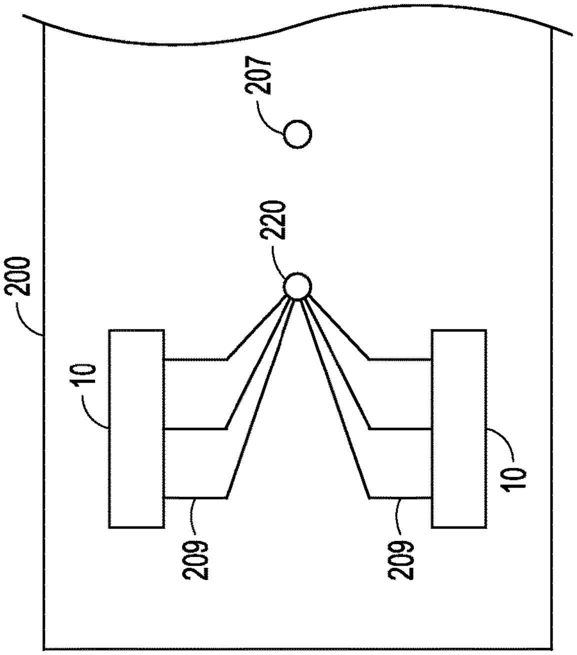
FIG. 2 shows a top view of a portion of a PCB, in accordance with one embodiment.
Figure 3:
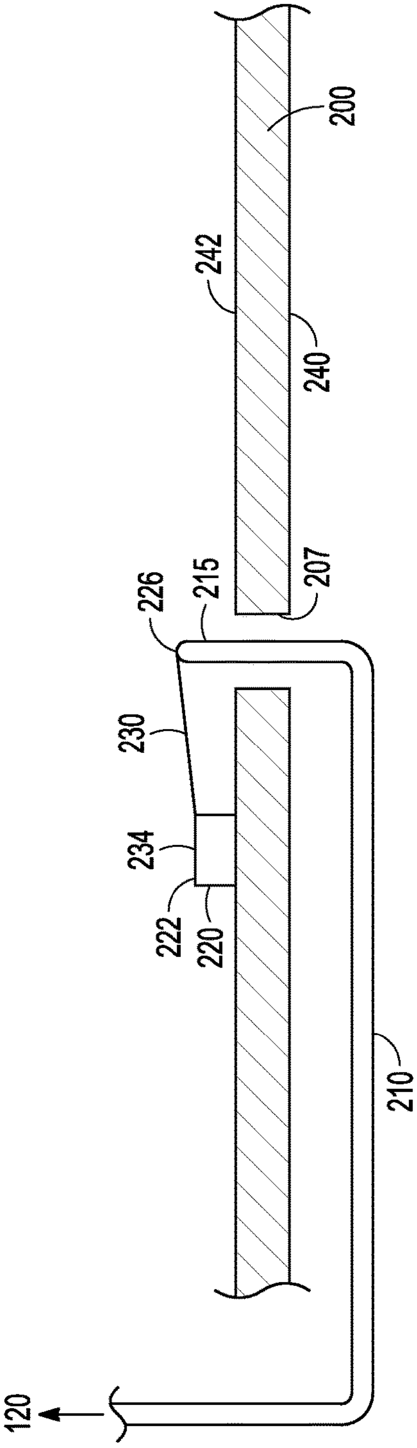
FIG. 3 shows a cross-section side view of the PCB, in accordance with one embodiment.
Figure 4:
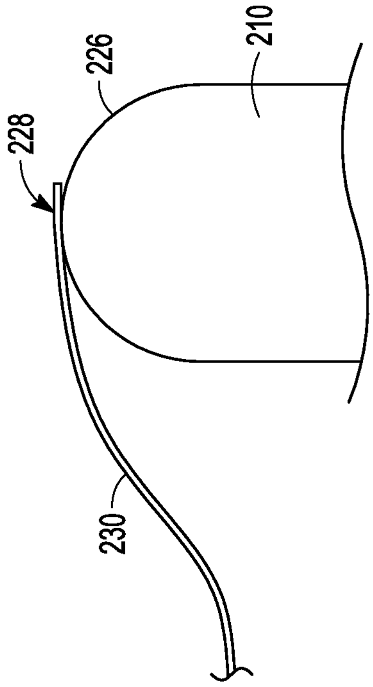
FIG. 4 shows a view of a feedthrough wire, in accordance with one embodiment.

FIG. 2 shows a top view of a portion of a PCB 200, in accordance with one embodiment; FIG. 3 shows a cross-section side view of the PCB 200, in accordance with one embodiment; and FIG. 4 shows a close-up view of a feedthrough wire 210, in accordance with one embodiment.

Here, the electronic devices of the pulse generator 105 can include the printed circuit board assembly (PCB 200) electronically connected to the header 112 (FIG. 1) by a feedthrough wire 210 running from the feedthrough assembly 120 to the PCB 200. One challenge is to make the connection to the PCB easier from a manufacturing point of view.

The PCB 200 can include the plurality of electronic components 10 connected to the PCB 200 and the PCB 200 can include a plurality of traces 209 and through holes 207 and contacts 220. For the sake of clarity, only one through hole, and a few traces, and components are show. In actual use, the PCB 200 can include a plurality of all the items.

As noted above, there is a need to ensure accurate placement of PCB components in regard to the space limitations. Moreover, robust and easy to make connections between the various components is desired.

As noted, the PCB 200 can be electronically connected to the header 112 by the feedthrough wire 210 running from the feedthrough assembly 120 to the PCB 200. In actual practice, a plurality of feedthrough wires 210 can run between the feedthrough assembly and the PCB 200, but for ease of explanation, only a single feedthrough wire 210 will be discussed.

The feedthrough wire 210 can extend through the through-hole 207 of the PCB 200 and can include a dome-shaped end 226 adapted to be attached to a connector ribbon 230 by laser wire bonding. The distal end of the feedthrough wire 210 including the dome shaped end 226 can also be described as a feedthrough pin 215. In one example, the feedthrough wire 210 can include a platinum feedthrough wire.

The dome-shaped end 226 of the feedthrough wire 210 can define a hemisphere shape at a distal end of the feedthrough wire 210. The dome-shaped end 226 is designed and configured to define a known contact point for the connector ribbon 230. This is because the highest point 228 or apex of the dome-shaped end 226 is the contact point for the connector ribbon 230. Thus, when the connector ribbon 230 is laid across the top surface of the feedthrough wire 210 at the dome-shaped end 226, the ribbon will contact the feedthrough wire 210 at the highest point 228 of the dome-shaped end 226. Then, when a user connects the connector ribbon 230 to the feedthrough wire 210, there is a known contact point between the two. This results in a consistent and quality connection. If the top of the feedthrough wire were flat, the connection might be made at various locations along the top surface, resulting in a less consistent connection. Also, a flat top can result in a gap between the ribbon and the top due to tolerance on the cut angle. This can result in blown or unstable welds. With the feedthrough wire having a dome shape end 226, the apex of the dome will provide a zero gap between the dome and the ribbon 230 and be in the same location every time.

Here, the feedthrough wire 210 extends from a bottom surface 240 of the PCB 200 and extends through the through-hole 207 of the PCB 200 such that the dome-shaped end 226 is exposed at an upper surface 242 of the PCB 200.

In one embodiment, the connector ribbon 230 can include an Nb (niobium) connector ribbon that can be connected to the feedthrough wire 210 using laser ribbon bonding. By utilizing laser ribbon bonding a more robust connection can be made, as compared to ultrasonic bonding for example.

A second end 234 of the connector ribbon 230 can be attached to the contact 220, which is electrically connected to the various traces 209. In this example, the contact 220 can include a contact pad 222, with the connector ribbon 230 attached to an upper surface of the contact pad 222. The contact pad 222 rises above a surface of the PCB 200.

Figure 5:
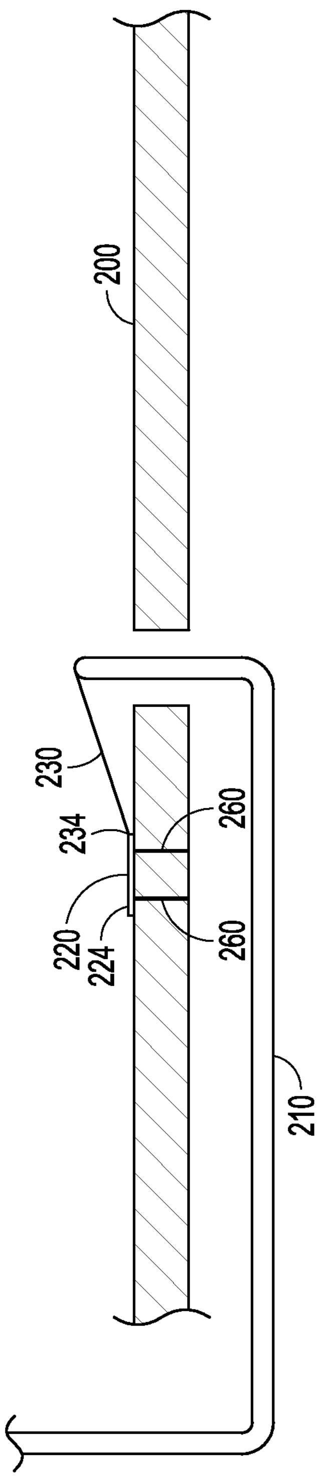
FIG. 5 shows a cross-section side view of the PCB, in accordance with one embodiment.
Figure 6:
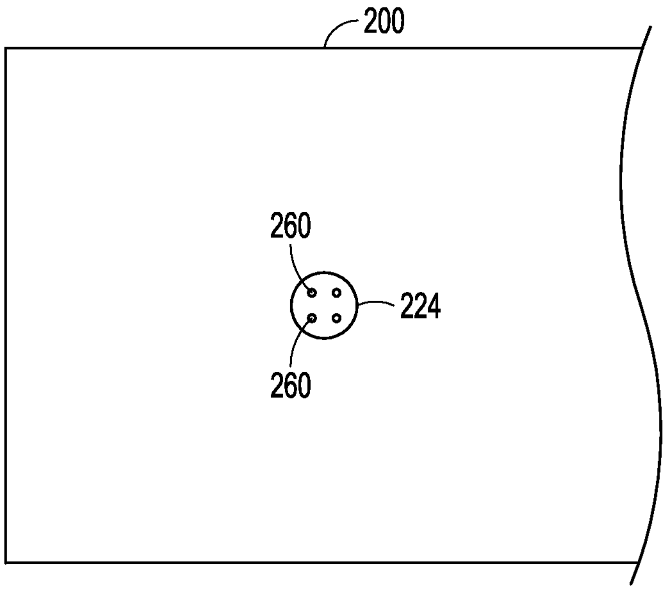
FIG. 6 shows a top view of the PCB, in accordance with one embodiment.

In one embodiment, the contact pad 222 can be omitted. For example, FIG. 5 shows a cross-section side view of the PCB 200, in accordance with one embodiment. FIG. 6 shows a top view of the PCB 200. Here, the second end 234 of the connector ribbon 230 is bonded directly to a surface contact 224 of the PCB 200. In this example, the contact pad 222 is omitted and the connector ribbon 230 is bonded directly to the surface contact 224. The surface contact 224 can be relatively flush to the surface 242 of the PCB 200 compared to the contact pad 222 of FIG. 3.

In one example, the surface contact 224 can include a copper substrate with a gold-coated contact surface. In an example, the gold-coating on the surface contact 224 can include a gold/nickel alloy. In this example, the connector ribbon can include a Nb material. Bonding a Nb connector ribbon 230 to the gold-plated contact 224 allows for direct surface bonding since the manufacturer only needs to heat the connection enough to make the gold melt. Such a connection works best with a Nb connector ribbon. In one example, the connector ribbon 230 can be bonded to the surface contact 224 by laser ribbon bonding.

In one example, the surface contact 224 can further include a plurality of vias 260 extending through surface contact 224 and extending through the PCB 200 from a top surface to a bottom surface of the PCB 200. The vias 260 provide for improved laser ribbon bonding to PCB 200 since the vias 260 provide for mechanical retention of the connector ribbon 230 and prevent the copper substrate from pulling away from the PCB surface when the bond is being made. Copper flowing within the vias 260 during bonding helps to hold the copper substrate to the PCB surface so that the copper substrate does not pull away from the PCB surface.

Figure 7:
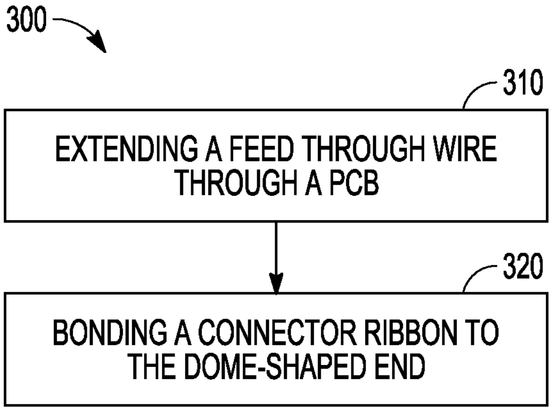
FIG. 7 shows a method of attaching a feedthrough wire to a connector ribbon, in accordance with one embodiment.

FIG. 7 shows a method (300) of attaching a feedthrough wire to a connector ribbon, in accordance with one embodiment. Referring also to FIGS. 2-6, the method (300) can include extending a feedthrough wire through a through-hole of a PCB (310), the feedthrough wire including a dome-shaped end, and bonding a connector ribbon to the dome-shaped end (320).

As discussed above, in some examples, the feedthrough wire can extend from a bottom surface of the PCB and extend through a through-hole of the PCB such that the dome-shaped end is exposed at an upper surface of the PCB. In one example, the bonding can include laser wire bonding.

In one example the method (300) can further include connecting the connector ribbon directly to a surface contact of the PCB, wherein the connector ribbon includes Nb, and the surface contact includes a gold-coated surface contact.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An implantable medical device comprising:

a housing including electronic devices and a PCB within the housing;

a header attached to the housing and including one or more bores; and a feedthrough assembly between the housing and the header;

a feedthrough wire extending from the feedthrough assembly through the PCB, the feedthrough wire including a dome-shaped end having an apex defining a singular contact point extending through the PCB, a connector ribbon laser wire bonded to the apex of the dome-shaped end of the feedthrough wire to connect the electronic devices to the feedthrough assembly wherein the dome-shaped end and the connector ribbon are disposed internal to the housing.

2. The implantable medical device of claim 1, wherein the feedthrough wire includes a platinum feedthrough wire.

3. The implantable medical device of claim 1, wherein the dome-shaped end of the feedthrough wire includes a hemisphere shape at a distal end of the feedthrough wire.

4. The implantable medical device of claim 1, wherein the feedthrough wire extends from a bottom surface of the PCB and extends through a through-hole of the PCB such that the dome-shaped end is exposed at an upper surface of the PCB.

5. The implantable medical device of claim 1, wherein the dome-shaped end is configured to define a known contact point for the connector ribbon.

6. The implantable medical device of claim 1, wherein the connector ribbon includes an Nb connector ribbon.

7. The implantable medical device of claim 6, wherein a second end of the connector ribbon is connected to a contact pad on the PCB.

8. The implantable medical device of claim 6, wherein a second end of the connector ribbon is bonded directly to a surface contact of the PCB.

9. The implantable medical device of claim 8, wherein the surface contact includes a copper substrate with a gold-coated contact surface.

10. The implantable medical device of claim 9, including a plurality of vias running through surface contact and the PCB.

11. An implantable medical device comprising:

a housing including electronic devices and a PCB within the housing;

a header attached to the housing and including one or more bores; and a feedthrough assembly between the housing and the header;

a feedthrough wire extending from the feedthrough assembly to the PCB, the feedthrough wire including a gold-coated contact surface; and a connector ribbon comprising Nb coupling a connector on the PCB to the feedthrough wire, wherein the Nb of the connector ribbon has a higher melting point than the gold-coated contact surface, enabling direct bonding to the gold-coated contact surface of the feedthrough wire.

12. The implantable medical device of claim 11, wherein the connector ribbon is bonded directly to a surface contact of the PCB.

13. The implantable medical device of claim 12, wherein the surface contact includes a copper substrate with a gold-coated contact surface.

14. The implantable medical device of claim 13, including a plurality of vias running through the surface contact and the PCB.

15. The implantable medical device of claim 14, wherein the connector ribbon is bonded to the surface contact by laser ribbon bonding.

16. The implantable medical device of claim 11, wherein the feedthrough wire is attached to the connector ribbon at a dome-shaped end of the feedthrough wire.

17. A method of attaching a feedthrough wire to a connector ribbon, the method comprising:

extending a feedthrough wire through a through-hole of a PCB, the feedthrough wire including a dome-shaped end having an apex defining a singular contact point; and bonding a connector ribbon to the apex of the dome-shaped end.

18. The method of claim 17, wherein the bonding includes laser wire bonding.

19. The method of claim 17, further comprising connecting the connector ribbon directly to a surface contact of the PCB, wherein the connector ribbon includes Nb and the surface contact includes a copper substrate with a gold-coated contact surface.

20. The method of claim 19, including a plurality of vias running through surface contact and the PCB.

* * * * *